United States Patent [19]

Freiberg

[11] 4,320,123

[45] Mar. 16, 1982

[54] ANIMAL SYSTEMIC INSECTICIDE

[75] Inventor: Ashley H. Freiberg, Santa Clara, Calif.

[73] Assignee: Stauffer Chemical Company, Westport, Conn.

[21] Appl. No.: 220,941

[22] Filed: Dec. 29, 1980

[51] Int. Cl.$^3$ ................ C07D 309/06; A61K 31/665
[52] U.S. Cl. ........................... 424/203; 260/345.9 R
[58] Field of Search ................ 260/345.9 R; 424/203

[56] References Cited

U.S. PATENT DOCUMENTS 3,318,915  5/1967  Hasserodt et al. ........... 260/345.9 R
4,058,606 11/1977  Kiehs et al. .................. 260/345.9 R

*Primary Examiner*—Nicky Chan
*Attorney, Agent, or Firm*—Beth Kovitz

[57] ABSTRACT

An animal systemic insecticide having the formula

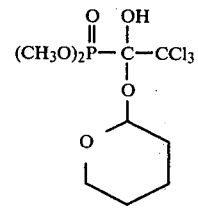

6 Claims, No Drawings

ANIMAL SYSTEMIC INSECTICIDE

FIELD OF THE INVENTION

This invention relates to O,O-dimethyl-2,2,2-trichloro-1-hydroxy-1(pyranyl-2-oxy)ethylphosphonate and its use as an animal systemic insecticide.

BACKGROUND OF THE INVENTION

An insecticide is a compound that controls insect life. Insect life may be controlled by killing a substantial proportion of an insect population. Compounds which control insect life in this manner must be highly toxic to the insect population and non-toxic to other living things.

Insecticides may be applied to an area where it is desired to control insect life by a variety of methods. These methods include topical application and systemic application.

Topical application is application of the insecticide directly to the area where the insect desired to be controlled is present or may light. Insecticides applied topically remain localized near the site of application.

By contrast, systemic insecticides are applied to a site remote from the area where the insect to be controlled is present or may light. A systemic insecticide is capable of freely translocating within a living body. The insecticide translocates within the living body from the site of application to the area where the insect to be controlled is present. The insect is killed in the area where it is present. The living body through which the insecticide has translocated remains unharmed.

Whatever the method of application, a certain minimum amount of a compound is effective to control insect life. This amount is the "insecticidally effective amount."

Insecticides are commonly used to control insects which are harmful to man. Insects may be harmful to man either directly, e.g. by carrying disease, or indirectly, e.g., by destroying animal life, plant life, food products, or other commodities.

Blowflies are an example of an insect which destroys animal life. Screwworm flies are a type of blowfly which present a particular problem.

Screwworms populate warm climates. They are found in the southern United States, including Texas, New Mexico and Arizona, and Central and South America. These insects are dangerous to cattle, hogs, horses, mules, sheep, goats, dogs and other domestic and wild animals.

Screwworms attack a host animal, e.g., cow, hog, etc., at an open wound or other diseased body opening and lay their eggs at the site of the opening. Screwworm larvae feed on the wound or opening and invade healthy tissue surrounding it. Infestation of an opening in this manner prevents the opening from healing.

The odor of an infested opening attracts additional flies, including other types of blowflies, to the opening. The newly attracted flies lay their eggs near the infested opening. Successive generations of insects cause a serious inflammation. Unless the blowfly infested opening is treated effectively, death of the host animal is inevitable.

To date, treatment of openings attacked by screwworms has been limited to application of a topical smear. Care must be taken to insure that the entire infested area has been completely covered by the smear. It is difficult to protect inaccessible areas of the animal in this manner.

DESCRIPTION OF THE INVENTION

This invention relates to O,O-dimethyl-2,2,2-trichloro-1-hydroxyl-(pyranyl-2-oxy) ethylphosphonate and its use as an animal systemic insecticide. This compound has the structure:

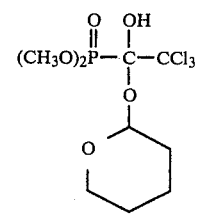

It has now been discovered that 2,2,2-trichloro-1-hydroxy-1-(pyranyl-2-oxy) ethylphosphonate is useful as an animal systemic insecticide for the control of blowfly infestations. An insecticidally effective amount of O,O-dimethyl-2,2,2-trichloro-1-hydroxy-1-(pyranyl-2-oxy) ethylphosphonate may be applied to an animal with a screwworm infested wound at a site remote from the area of screwworm attack, e.g. by feeding, and will kill the screwworms at the wound location.

PREPARATION

O,O-dimethyl-2,2,2-trichloro-1-hydroxy-1-(pyranyl-2-oxy) ethylphosphonate was prepared by the following procedure.

Ten (10) grams (g) of O,O-dimethyl-2,2,2-trichloro-1-hydroxy ethylphosphonate having the structure:

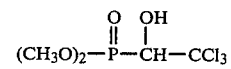

was dissolved in 50 milliliters (ml) of benzene and 20 ml of dihydropyran. A drop of concentrated sulfuric acid was added and the mixture was warmed to 40° C. and maintained at that temperature for ½ hour.

The O,O-dimethyl-2,2,2-trichloro-1-hydroxy-1-(pyranyl-2-oxy) ethylphosphonate was washed with sodium bicarbonate, dried and stripped. $n_D^{30} = 1.4920$. Structure was confirmed by infrared (IR) spectroscopy.

TESTING

O,O-dimethyl-2,2,2-trichloro-1-hydroxy-1-(pyranyl-2-oxy) ethylphosphonate was administered orally by stomach tube to mice. After treatment, the animals were sacrificed and muscle tissue was taken for bioassay with blowfly larvae. The blowfly larvae were allowed to feed on the muscle tissue excised from the treated mice. Systemic activity was evaluated as a function of larval mortality after the larvae had fed on the tissue.

The average percent larval mortality at 100, 200 and 400 milligrams of O,O-dimethyl-2,2,2-trichloro-1-hydroxy-1-(pyranyl-2-oxy) ethylphosphonate per kilogram of mouse weight was 100%. The number of mice treated at each dosage was two. The O,O-dimethyl-2,2,2-trichloro-1-hydroxy-1-(pyranyl-2-oxy) ethylphosphonate did not kill any of the mice.

TEST RESULTS

O,O-dimethyl-2,2,2-trichloro-1-hydroxy-1-(pyranyl-2-oxy) ethylphosphonate was translocated through the bodies of the mice to muscle tissue and was effective to kill blowfly larvae after translocation. The compound was non-toxic to the mice.

FORMULATIONS

A formulation is the incorporation of an active ingredient in a form which may be administered directly to an animal. In this case, the active ingredient is O,O-dimethyl-2,2,2-trichloro-1-hydroxy-1-(pyranyl-2-oxy) ethylphosphonate.

O,O-dimethyl-2,2,2-trichloro-1-hydroxy-1-(pyranyl-2-oxy) ethylphosphonate may be formulated by impregnation on an inert carrier or agent. The formulated O,O-dimethyl-2,2,2-trichloro-1-hydroxy-1-(pyranyl-2-oxy) ethylphosphonate may then be incorporated on or in an animal's feed supply for ingestion by the animal.

What is claimed is:

1. O,O-Dimethyl-2,2,2-trichloro-1-hydroxy-1-(pyranyl-2-oxy) ethylphosphonate.
2. A method of killing insect larvae in an animal having an opening infested with said larvae comprising administering an insecticidally effective amount of O,O-dimethyl-2,2,2-trichloro-1-hydroxy-1-(pyranyl-2-oxy) ethylphosphonate to said animal.
3. A method as defined in claim 2 wherein said insects are blowflies.
4. A method as defined in claim 3 wherein said blowflies are screwworm flies.
5. A method as defined in any of claims 2, 3, or 4 wherein said O,O-dimethyl-2,2,2-trichloro-1-hydroxy-1-(pyranyl-2-oxy) ethylphosphonate is administered by feeding.
6. A composition comprising an insecticidally effective amount of O,O-dimethyl-2,2,2-trichloro-1-hydroxy-1-(pyranyl-2-oxy) ethylphosphonate formulated with an inert diluent carrier or agent.

* * * * *